(12) United States Patent
Kerwin (10) Patent No.: US 7,294,643 B2
(45) Date of Patent: Nov. 13, 2007

(54) UK-1 ANALOGUES: METHODS OF PREPARATION AND USE

(75) Inventor: Sean M. Kerwin, Round Rock, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 650 days.

(21) Appl. No.: 10/720,991

(22) Filed: Nov. 24, 2003

(65) Prior Publication Data

US 2005/0004188 A1    Jan. 6, 2005

Related U.S. Application Data

(60) Provisional application No. 60/428,379, filed on Nov. 22, 2002.

(51) Int. Cl.
*A61K 31/423*   (2006.01)
*A61K 31/195*   (2006.01)
*C07C 233/66*   (2006.01)
*C07D 263/56*   (2006.01)
*C07D 263/57*   (2006.01)

(52) U.S. Cl. ............. 514/375; 514/613; 548/224; 564/161

(58) Field of Classification Search ........ 548/224; 514/375, 613; 564/161
See application file for complete search history.

(56) References Cited

OTHER PUBLICATIONS

Dunwell, David et al, "Synthesis & Antiinflammatory Activity of Some 2-aryl-6-benzoxazoleacetic Acid Derivatives," J. Med. Chem, 1977, 20 (6), pp. 797-801.*
DeLuca et al., "The Total Synthesis of UK-1", Tetrahedron Letters, 38:2(1997) 199-202.
Ahmed et al., "A new rapid and simple non-radioactive assay to monitor and determine the proliferation of lymphocytes: an alternative to [$^3$ H] thymidine incorporation assay", Journal of Immunological Methods, 170(1994) 211-224.
Likussar et al., "Theory of Continuous Variations Plots and a New Method of Spectophotometric Determination of Extraction and Formation Constants", Analytical Chemistry, 43:10(1971) 1265-1272.

* cited by examiner

*Primary Examiner*—Joseph K. McKane
*Assistant Examiner*—Janet L. Coppins
(74) *Attorney, Agent, or Firm*—Meyertons, Hood, Kivlin, Kowert & Goetzel, P.C.; Eric B. Meyertons (57) ABSTRACT

The present invention includes a number of structural analogues of UK-1. A comparision of the anticancer activity of the UK-1 analogues with their ability to inhibit the growth of methicillin-sensitive and methicillin-resistant *Staphylococcus aureus* demonstrates that a structurally simplified analogue of UK-1 retains the natural product's selective activity against cancer cells. Structurally conservative changes to UK-1 that diminish $Mg^{2+}$-binding ability may result in a dramatic decrease in cancer cell cytotoxicity. The results may establish a minimum structural pharmacophore as well as a functional role for $Mg^{2+}$-binding in the selective cytotoxicity of UK-1.

6 Claims, 3 Drawing Sheets

UK-1 ANALOGUES: METHODS OF PREPARATION AND USE

PRIORITY CLAIM

This application claims priority to Provisional Patent Application No. 60/428,379 entitled "UK-1 ANALOGUES: METHODS OF PREPARATION AND USE" filed on Nov. 22, 2002.

BACKGROUND OF THE INVENTION

1. Field of the Invention

The present invention generally relates to bis(benzoxazole) compositions and methods of making the compositions. More particularly, the invention relates to analogues of natural occurring bis(benzoxazole) compositions and methods of making bis(benzoxazole) analogues.

2. Description of the Relevant Art The relatively simple yet novel bis(benzoxazole) natural products UK-1 and AJ19561 represent a new class of cytotoxic secondary metabolites. Interest in this class of bis(benzoxazoles) is fueled by the finding that UK-1 is selectively cytotoxic to cancer cells but not bacterial cells, yeast, or fungi. This selective cytotoxicity may be mediated through the specific interaction of UK-1 with an as yet undefined cancer cell-associated target. Bis(benzoxazole) natural products are a structurally unique class of Streptomyces secondary metabolites that have recently been reported in the literature. Research groups have isolated UK-1 from acetone extracts of Streptomyces sp. 517-02.

UK-1

Research groups have isolated AJI9561 from Streptomyces sp. AJ956.

AJI9561

UK-1 and AJI9561 were reported to possess growth inhibitory properties against murine cancer cell line P388, with $IC_{50}$ values from 0.3–1.6 μM. While UK-1 has cancer cell cytotoxic properties, UK-1 does not inhibit the growth of gram-positive or gram negative bacteria, yeast, or fungi at concentrations as large as 250 μM.

The selective cytotoxicity of UK-1 towards cancer cells versus bacteria and fungi indicates that UK-1 may have a unique mechanism of anticancer action. The 2-(2'-hydroxyphenyl) benzoxazole moiety present in UK-1 is also present in a number of synthetic metal ion chelators and is analogous to the 2-(2'-hydroxyphenyl)oxazole moiety present in a class of microbial siderophores.

The cytotoxicity of UK-1 against P388, B 176, and HeLa cell lines have been previously reported.

Cytotoxicity of UK-1 against Cancer Cell Lines.

| Cell Line | $IC_{50}$[a] |
|---|---|
| MCF-7 | 1.6 μM |
| HT-29 | 65 μM |
| HL60 | 0.32 μM |
| PC-3 | 0.4 μM |
| MDA-231 | 0.5 μM |
| BT-20 | 0.17 μM |
| DU145 | 0.2 μM |
| SKBR3 | 0.1 μM |
| A549 | 1.9 μM |
| SK-N-AS | 24 μM |
| SK-N-D7 | 0.17 μM |
| SK-N-F1 | 7 μM |
| SK-N-MC | 1.1 μM |
| SK-N-SH | 7 μM |
| CHP-212 | 12 μM |
| IMR-32 | 0.06 μM |
| NGP | 0.02 μM |

[a]determined using the alamarBlue assay. See Examples for details.

UK-1 displays a wide spectrum of potent anticancer activity against leukemia, lymphoma, and certain solid tumor-derived cell lines. In particular, certain neuroblastoma cell lines (IMR-32 and NGP) were very sensitive to UK-1, with $IC_{50}$ values less than about 100 nM. Other cell lines, such as colon (HT-29), were less sensitive. Despite the potential anticancer activity, there was no indication of any antibacterial effect against Staphylcoccus aureus, methicillin-resistant S. aureus, or Pseudomonas aeruginosa at concentrations up to 50 μg/mL of UK-1.

The metal ion binding ability of synthetically prepared UK-1 has also been investigated. The studies indicate that UK-1 is capable of binding a variety of biologically important metal ions, of particular interest, $Mg^{2+}$ ions. UK-1 binds DNA in a metal ion-dependent fashion like the $Mg^{2+}$ binding aureolic acid group of antitumor antibiotics and synthetic antitumor quinobenzoxazines. One consequence of the interaction of UK-1 with DNA is the inhibition of topoisomerase II.[9] A more recent investigation of the metal mediated double strand DNA (ds) binding by Electrospray Ionization Mass Spectrometry (ESI-MS) demonstrated that UK-1 forms complexes of the type [ds+UK-1+$M^{2+}$] with a variety of metals, such as $Ni^{2+}$, $Co^{2+}$, and $Zn^{2+}$. The results distinguish the metal mediated DNA binding of UK-1 with the observed metal mediated DNA binding of aureolic acids and quinobenzoxazines. Aureolic acids form metal mediated DNA binding complexes of the form [ds+2× ligand+$M^2$+]. Quinobenzoxazines bind as [ds+2× ligand+2×M2+] metal mediated DNA binding complexes.

The semi-synthetic derivatives methyl UK-1 (MUK-1) and demethyl UK-1 (DMUK-1) both have shown activity against Gram-positive and Gram-negative bacteria. MUK-1 also is active against yeast and filamentous fungi.

SUMMARY OF THE INVENTION

A series of analogues of the bis(benzoxazole) natural product UK-1 in which the carbomethoxy-substituted benzoxazole ring of the natural product was modified were prepared. Some UK-1 analogues may have important anticancer and antibacterial properties. An analogue of UK-1 in which the carbomethoxy-substituted benzoxazole ring was replaced with a carbomethoxy-substituted benzimidazole ring was inactive against human cancer cell lines and the two strains of *S. aureus*. In contrast, a simplified analogue in which the carbomethoxy-substituted benzoxazole ring was replaced with a carbomethoxy group was almost as active as UK-1 against the four cancer cell lines examined, but lacked activity against *S. aureus*. Metal ion binding studies of the UK-1 analogues demonstrate that they both bind $Zn^{2+}$ and Ca ions about as well as UK-1. The non-cytotoxic benzimidazole UK-1 analogue binds $Mg^{2+}$ ions 50-fold weaker than UK-1, whereas the simple benzoxazole analogue binds $Mg^{2+}$ ions nearly as well as UK-1. $Mg^{2+}$ ion binding may play a role in the selective cytotoxicity of UK-1 and may provide a minimal pharmacophore for the selective cytotoxic activity of the natural product.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawing and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

A number of UK-1 analogues were prepared in which the carbomethoxy-substituted benzoxazole ring was either modified or deleted. In some embodiments, the synthesis of UK-1 analogues was carried out in analogy with the published synthesis technique for the natural product UK-1, with some improvements. The techniques were published in the paper "The total synthesis of UK-1" to DeLuca and Kerwin Tetrahedron Lett. 1997, 38, 199-202, which is incorporated herein by reference.

A UK-1 analogue may be of the general structure, I:

In some embodiments, A is a substituent of the form, Ia:

In some embodiments, A is a substituent of the form, Ib:

B may be $CO_2R^3$, $CON(R^4)_2$, 2-benzoxazoyl, 2-benzothiazoyl group optionally substituted with $CO_2R$, $CON(R^4)_2$, and/or any other group that imparts $Mg^{2+}$ binding ability. Each occurance of R, $R^1$, $R^2$, $R^3$, $R^4$ may be independently, but is not limited to: H, alkyl, halo, haloaklyl, alkoxy, alkylamino, amino acid, peptide, $COOR^4$, and/or $COR^4$. In some embodiments, n may be between 0 and 4. In some embodiments, X may be $NR^3$. X may be O and/or S. In an embodiment, Y is CH. Y may be $CR^2$ and/or N.

In some embodiments, A is a substituent of the form, Ia:

wherein Y is CH, CR$^1$, or N;
wherein n is 1 to 3; and
wherein each R$^1$ is independently H, alkyl, halo, haloalkyl, alkoxy, arylalkyl, or alkylamino, and wherein R$^1$ is positioned on any carbon ortho, meta, or para to the —OH group. In one embodiment, R$^1$ is a benzyl group in an ortho position to with respect to the —OH group.

Figure 1:
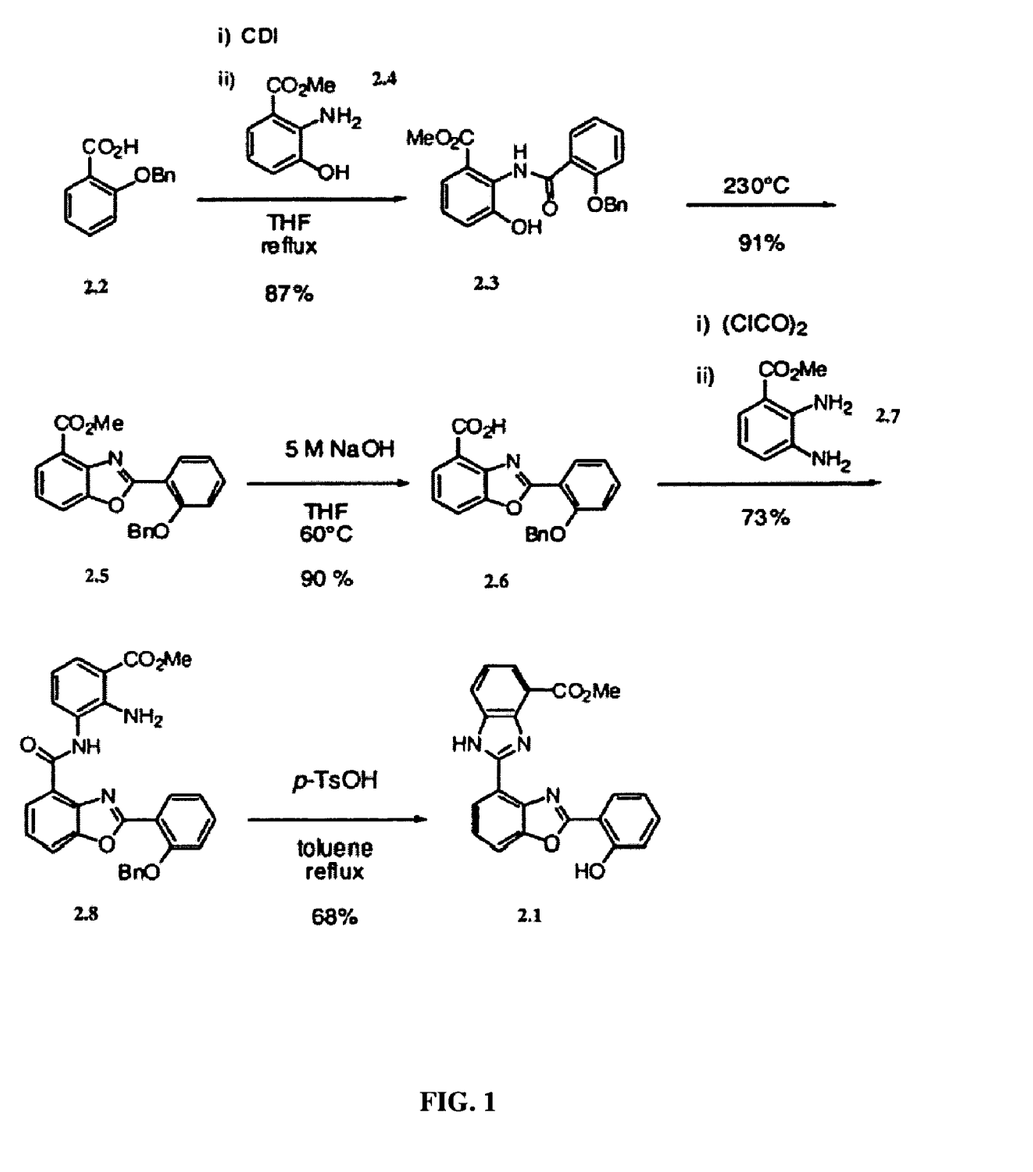
FIG. 1 depicts an embodiment of a method of forming compound 2.1.

In an embodiment, the UK-1 analogue, compound 2.1, is formed when a substituted benzimidazole ring replaces the carbomethoxy-substituted benzoxazole ring of UK-1. In some embodiments, compound 2.1 may be prepared as shown in FIG. 1. As shown in FIG. 1, carbonyl diimidazole-coupling of 2-(benzyloxy)benzoic acid, 2.2, with methyl anthranilic acid, 2.4, produces amide 2.3. The pyrolysis of amide 2.3 at 230° C., under vacuum produces benzoxazole 2.5. Benzoxazole 2.5 reacts with NaOH and THF at 60° C. to produce benzoxazole acid 2.6. Coupling benzoxazole acid 2.6 with methyl 2,3-diaminobenzoate, 2.7, yields amide 2.8. A final cyclodehydration and deprotection yields compound 2.1. Compound 2.1 is produced by heating amide 2.8 in the presence of p-toluenesulfonic acid (p-TsOH). Compound 2.1 may be produced with a 35% overall yield from 2-benzyloxybenzoic acid.

Figure 2:
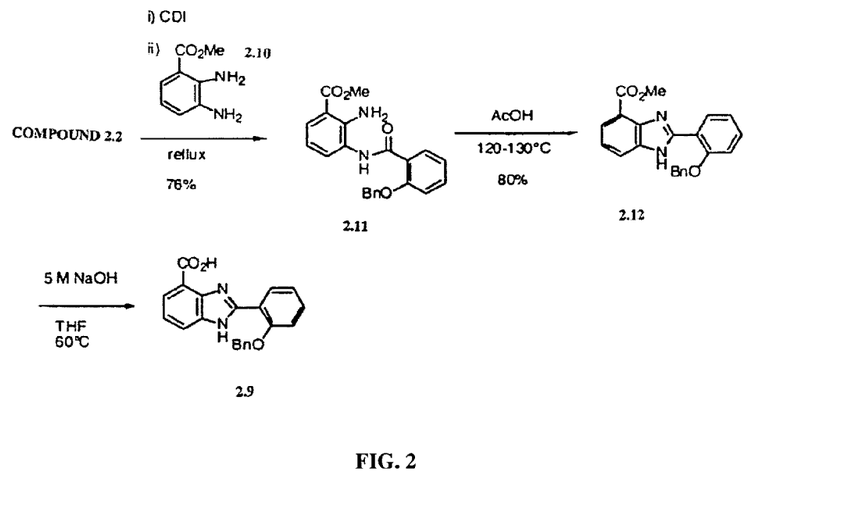
FIG. 2 depicts an embodiment of a method of forming compound 2.9.

In an embodiment, the UK-1 analogue, compound 2.9, may be a simple benzimidazole analogue. In some embodiments, compound 2.9 may be prepared as shown in FIG. 2. As shown in FIG. 2, condensation of 2-benzyloxybenzoic acid, 2.2, with methyl 2,3-diaminobenzoate, 2.10, yielded amide 2.11 with a yield of about 76%. Amide 2.11 may be cyclized by heating in acetic acid at a temperature of about of about 120° C.-130° C. to give benzimidazole ester 2.12. Compound 2.9 may be produced by the hydrolysis of benzimidazole ester 2.12. Hydrolysis of the benzimidazole 2.9 may be performed by heating in the presence of NaOH and THF. Compound 2.9 may be produced with an overall yield of 49%.

Figure 3:
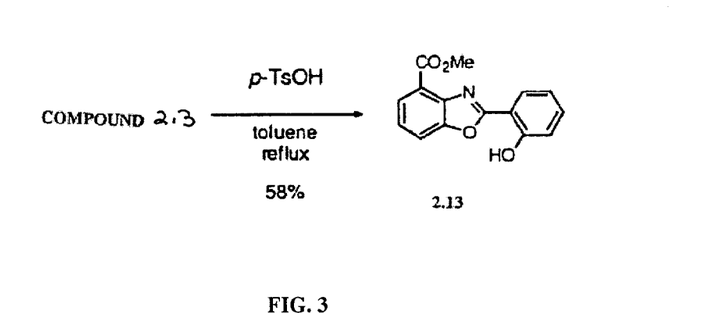
FIG. 3 depicts an embodiment of a method of forming compound 2.13.

The UK-1analogue may be a substituted benzoxazole, compound 2.13. In an embodiment, compound 2.13 may be produced by the method shown in FIG. 3. As shown in FIG. 3, Amide 2.3, produced by the method shown in FIG. 1, may be reacted with p-TsOH and toluene to yield compound 2.13. Compound 2.13 may be prepared by p-TsOH mediated cyclization and deprotection.

Figure 4:
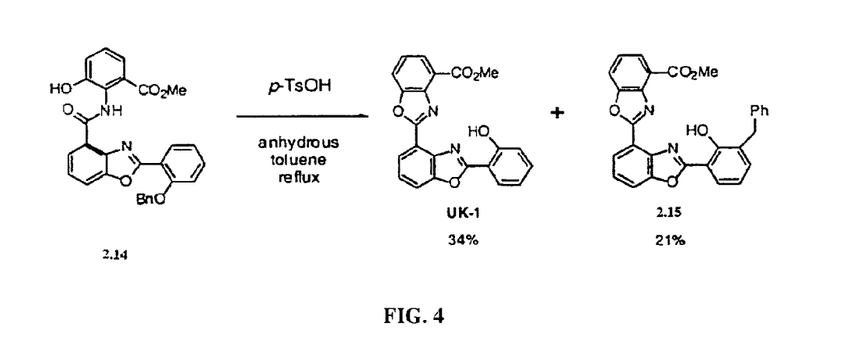
FIG. 4 depicts an embodiment of a method of forming compound 2.15.

The UK-1analogue may be a benzlyated UK-1analogue, compound 2.15. Compound 2.15 may be synthesized by the method shown in FIG. 4. As shown in FIG. 4, when the cyclization/deprotection shown in FIG. 3 is performed under anhydrous conditions, compound 2.15 is produced as a side product. Compound 2.15 may be produced as a side product in the synthesis of UK-1. Compound 2.15 may arise from the interception of a benzyl cation formed by acid-mediated cleavage of the benzyl ester. In other methods of preparation of UK-1, the benzyl cation may be intercepted by adventitious water in the reaction mixture. Under more anhydrous conditions, the benzyl cation may be able to participate in Friedel-Crafts alkylation chemistry, producing compound 2.15. In an embodiment, UK-1analogue 2.15 may not be formed if the UK-1 synthesis of FIG. 4 takes place in the presence of 2-4 equivalents of water.

Cancer Cell Cytotoxicity and Antibacterial Activity of UK-1 Analogues

The cancer cell cytotoxicity and antibacterial activity of UK-1 analogues was examined in order to determine the structural basis for the unique cancer cell selective cytotoxicity of UK-1. Benzoxazole, 2.16, and 2-(2'-hydrophenyl)benzoazole, 2.17, were also examined.

2.16: Benzoxazole 2.17: 2-(2'-hydrophenyl)benzoazole

Antibacterial and Anticancer Activity of UK-1 and Analogues.

| Compound | Antibacterial IC$_{50}$[a] | | Cytotoxicity IC$_{50}$ Range[b] |
|---|---|---|---|
| | S. aureus | Meth-resist S. aureus | |
| UK-1 | NA[c] | NA[c] | 0.32-65 µM |
| 2.15 | nd[d] | nd[d] | 4.5-27 µM |
| 2.1 | NA | NA | 70->100 µM |
| 2.5 | NA | NA | >100 µM |
| 2.6 | 43 µM | 29 µM | >100 µM |
| 2.9 | 102 µM | 102 µM | >100 µM |
| 2.13 | NA | NA | 0.88-9.1 µM |
| 2.16 | NA | NA | >100 µM |
| 2.17 | NA | NA | >100 µM |
| Ciprofloxacin | 0.45 µM | 0.45 µM | nd |
| Mitomycin C | nd | nd | 0.08-0.27 µM |

[a]Sample concentration that affords 50% growth of the test organism.
[b]Range of IC$_{50}$ values obtained by alamarBlue cytotoxicity assays against MCF-7, HL-60, HT-29, and PC-3 cells after 72 h at 37° C.
[c]No activity observed at concentrations up to 50 µg/mL.
[d]Not determined.

The above table shows the results of cytotoxicity testing against MCF-7, HT-29, HL60, and PC-3 cell lines along with the antibacterial assays against S. aureus and a methicillin-resistant strain of S. aureus. UK-1 shows a wide range of cytotoxic activity against the four cancer cell lines. This cytotoxic activity may be due to the relative resistance of the HT-29 cells to the action of UK-1. The benzylated UK-1analogue, compound 2.15, demonstrates a diminished cytotoxic effect against the cancer cell lines relative to UK-1; however, the spectrum of activity of compound 2.15 is quite distinct. Compound 2.15 is more active than UK-1 against HT-29 cells (IC$_{50}$ 5.2 µM for compound 2.15 versus 65 µM for UK-1). Compound 2.15 is about ten-fold less potent against MCF-7 (IC$_{50}$ 13 µM for compound 2.15 versus IC$_{50}$ 1.6 µM for UK-1, respectively) and PC-3 cells (IC$_{50}$ 4.5 µM for compound 2.15 versus $IC_{50}$ 0.4 µM for UK-1, respectively). Compound 2.15 is twenty-fold less active than UK-1 against HL60 cells ($IC_{50}$ 27 µM for compound 2.15 versus 0.32 µM for UK-1). Compound 2.15 has different bacterial cell selectivity properties than UK-1.

The aza-analogue of UK-1, compound 2.1, does not exhibit anticancer activity against three of the four cell lines examined, with $IC_{50}$ values greater than approximately 100 µM against MCF-7, HT-29, and PC-3 cells. Compound 2.1 did demonstrate very modest activity against HL60 cells ($IC_{50}$=70 µM). Compound 2.1 may lack antibacterial activity against the two strains of S. aureus examined. Many other analogues of UK-1 also appeared to lack appreciable anticancer activity. Two analogues, compound 2.6 and compound 2.9, displayed some antibacterial activity against S. aureus strains. The activity of compounds 2.6 and 2.9 against S. aureus, while modest, is unexpected in light of the reported antibacterial activity of DMUK-1 and the apparent lack of antibacterial activity of methyl ester UK-1, compound 2.5, and the methyl ester of compound 2.4. Compound 2.17, 2-(2'-hydroxyphenyl)benzoxazole, is neither cytotoxic to cancer cells nor antibacterial, in conformity with previous reports of the lack of antibacterial activity for compound 2.17.

Compound 2.13 demonstrated cancer cell cytotoxicity. Compound 2.13 also displayed the selective activity against cancer cells versus bacterial cells that is characteristic of the natural product, UK-1. The anticancer activity of compound 2.13 appears to be less than UK-1 against HL60 ($IC_{50}$=5.7 1M for compound 2.13 versus $IC_{50}$=0.4 µM for UK-1) and PC-3 cells ($IC_{50}$=0.88 µM for compound 2.13 versus $IC_{50}$=0.32 µM for UK-1). The anticancer activity for compound 2.13 appears to be equal to or better than UK-1 against MCF-7 ($IC_{50}$=1.5 µM for compound 2.13 versus $IC_{50}$=1.6 µM for UK-1) and HT-29 cells ($IC_{50}$=9.1 µM for compound 2.13 versus $IC_{50}$=65 µM for UK-1). Compound 2.13 does not appear to be active against S. aureus, P. aeruginosa, Cryptococcus neoformans, or Candida albicans ($IC_{50}$ greater than 50 µg/mL)

Metal Binding of UK-1 Analogues

Association Constants for Metal Ion Binding by UK-1 and Analogues.

|  | Compound | | |
| --- | --- | --- | --- |
| Metal Ion | UK-1 | 2.1 | 2.13 |
| $Mg^{2+}$ | $2.0 \times 10^6$ $M^{-1}$ | $4.0 \times 10^4$ $M^{-1}$ | $3.2 \times 10^5$ $M^{-1}$ |
| $Ca^{2+}$ | $4.0 \times 10^4$ $M^{-1}$ | $1.0 \times 10^5$ $M^{-1}$ | $6.3 \times 10^3$ $M^{-1}$ |
| $Zn^{2+}$ | $2.0 \times 10^6$ $M^{-1}$ | $3.2 \times 10^6$ $M^{-1}$ | $1.3 \times 10^6$ $M^{-1}$ |
| $Fe^{3+}$ | $2.5 \times 10^5$ $M^{-1}$ | $1.0 \times 10^4$ $M^{-1}$ | $7.9 \times 10^3$ $M^{-1}$ |

Previous work indicated the metal ion binding mechanism of UK-1, so the method of continuous variation was used to determine the ability of selected UK-1 analogues to bind a variety of metal ions. Methanolic solutions of UK-1 or UK-1 analogues and metal ion salts [$Ca(NO_3)_2$, $Mg(NO_3)_2$, $Zn(NO_3)_2$, or $Fe(NO_3)_3$] at various molar ratios, and 20 µM combined total concentration, were prepared and the absorbance at 418 nm was determined. Plots of $A_{418\ nm}$ versus mole ratio of ligand demonstrated maxima at 0.5 mole ratio for all metal ions, indicating a 1:1 stoichiometry for each of the metal ion complexes. Compound 2.1, which appears to lack cancer cell cytotoxicity, does not bind $Mg^{2+}$ and $Fe^{3+}$ ions as well as UK-1. Compound 2.1 does bind with $Ca^{2+}$ and $Zn^{2+}$ better than UK-1.

Compound 2.13, which appears to have cancer cell cytotoxic properties, retains similar $Zn^{2+}$ metal ion binding ability of UK-1. Compound 2.13 appears to have slightly diminished, relative to UK-1, $Mg^{2+}$, $Ca^{2+}$, and $Zn^{2+}$, binding ability

An appropriate 4-substituent on the 2-(2'-hydroxyphenyl)benzoxazole core may be important for efficient $Mg^{2+}$ binding ability. The 4-unsubstituted 2-(2'-hydroxyphenyl)benzoxazole, compound 2.17, does not appear to complex $Mg^{2+}$ ions. Compound 2.17 does appear to form complexes with $Zn^{2+}$.

The introduction of a 4-carbomethoxy substituent, as in compound 2.13, on the (2'-hydroxyphenyl)benzoxazole core imparts $Mg^{2+}$ ion binding ability. A 4-(benzoxazo-2-yl) substituent, as in UK-1 and compound 2.1, on the (2'-hydroxyphenyl)benzoxazole core does not appear to impart $Mg^{2+}$ ion binding ability. $Mg^{2+}$ ion binding may play a role in cancer cell cytotoxicity of UK-1 analogues. Cytotoxic UK-1 and compound 2.13 may bind $Mg^{2+}$ ions better than the less cytotoxic analogues, compounds 2.1 and 2.17. The selective activity of compound 2.13 against cancer cells, but not bacteria, may reflect a selective activity similar to UK-1. In some embodiments, compound 2.13 may be a minimum pharmacophore for the selective anticancer activity of UK-1.

The structural basis for $Mg^{2+}$ ion binding and selective cytotoxicity of UK-1 may be the same. Both $Mg^{2+}$ ion binding and selective cytotoxicity may require an appropriately 4-substituted 2-(2'-hydrophenyl)benzoxazole moiety. While it is unlikely that $Mg^{2+}$ ion binding per se is the origin of the selective cytotoxicity of UK-1 and analogue 2.13, the ability of UK-1 to form metal ion complexes that can bind to DNA and inhibit DNA-processing enzymes indicates that $Mg^{2+}$ ion binding by UK-1 may lead to biologically relevant complexes with a specific target in cancer cells.

As discussed above, certain non-covalent associations between UK-1 or UK-1 analogs and DNA are correlated with the selective cytotoxicity of these compounds towards cancer cell lines. In particular, metal-ion mediated complexation between UK-1 and UK-1 analogs with DNA is important in predicting the biological activity of the natural product. UK-1 and related analogs that are selectively cytotoxic, associate with double-stranded DNA more strongly in the presence of certain metal ions, such as $Mg^{2+}$ $Ni^{2+}$, $Cu^{2+}$, $Zn^{2+}$, or $Co^{2+}$. In contrast, analogs of UK-1 that are antibacterial associate with double-stranded DNA in a metal ion-independent fashion. This later behavior is similar to that displayed by antibacterial gyrase-inhibiting drugs such as ciprofloxacin. Finally, UK-1 analogs that are neither antibacterial nor cytotoxic fail to bind to double-stranded DNA, regardless of the presence or absence of divalent metal ions. This discovery provides a rapid and convenient method to screen for compounds with potential anticancer activity (e.g., those that bind to DNA in a metal ion-dependent fashion) or compounds that have potential antibacterial use (e.g., those that bind to DNA in a metal ion-independent fashion), and to distinguish these compounds from those that are not antibacterial or anticancer (e.g., those that do not bind to DNA in the presence or absence of metal ions).

Cancer Cell Cytotoxicity, Antibacterial Activity, and DNA Binding Ability of UK-1 and Analogs

| | Staph. aureus[a] IC$_{50}$ | Cytotoxicity[b] IC$_{50}$ | DNA-Binding ESI-MS[c] |
|---|---|---|---|
|  | >50 μg/mL | 0.32-65 μM | Metal Depend.[d] |
|  | >50 μg/mL | >100 μM | None[e] |
|  | >50 μg/mL | 0.88–9.1 μM | Metal Depend.[d] |
|  | 29 μg/mL | >100 μM | Metal Independ.[f] |
| Ciprofloxacin | 0.45 μg/mL | >100 μM | Metal Independ.[f] |

[a]concentration that inhibits the growth of Methacilline-resistant *Staph. Aureus* by 50%.
[b]range of concentrations required to inhibit the growth of MCF-7, HT-29, and PC-3 cells by 50% as determined by the alamarBlue assay.
[c]formation of ligand-DNA complex ions in the ESI-MS of ligand and double-stranded DNA oligonucleotide solutions in the presence or absence of added NiCl$_2$.
[d]all ligand-DNA complex ions also contained a metal ion.
[e]no ligand-DNA complex ions observed.
[f]ligand-DNA and ligand-DNA-metal ion complex ions observed.

We have also found that UK-1 can cleave DNA in the presence of oxidizing agents or in the presence of oxidizing agents and metal ions. Supercoiled ΦX174 DNA (50 μM) was incubated for 24 hrs in pH 8 Tris buffer (10 mM) at 37° C. with UK-1 (15-25 μM), H$_2$O$_2$ (5 μM-5 mM), or NiCl$_2$ (15-25 μM), or a combination of these agents.

Agarose gel electrophoresis was carried out to resolve the DNA products. There was no evidence of DNA cleavage in the samples containing only NiCl$_2$ or UK-1. There was an increase in the proportion of nicked, relaxed DNA product in the presence of an oxidant (e.g., H$_2$O$_2$), but no linear DNA that would indicate double-stranded DNA cleavage. However, in the presence of both UK-1 and an oxidant (e.g., H$_2$O$_2$), there was significantly more DNA cleavage, and linear DNA products were observed, indicating both single- and double-stranded DNA cleavage. The combination of UK-1, H$_2$O$_2$, and NiCl$_2$ was particularly active in inducing DNA cleavage, affording more relaxed and linear DNA products than control reactions that contained only H$_2$O$_2$ and NiCl$_2$.

Figure 5:
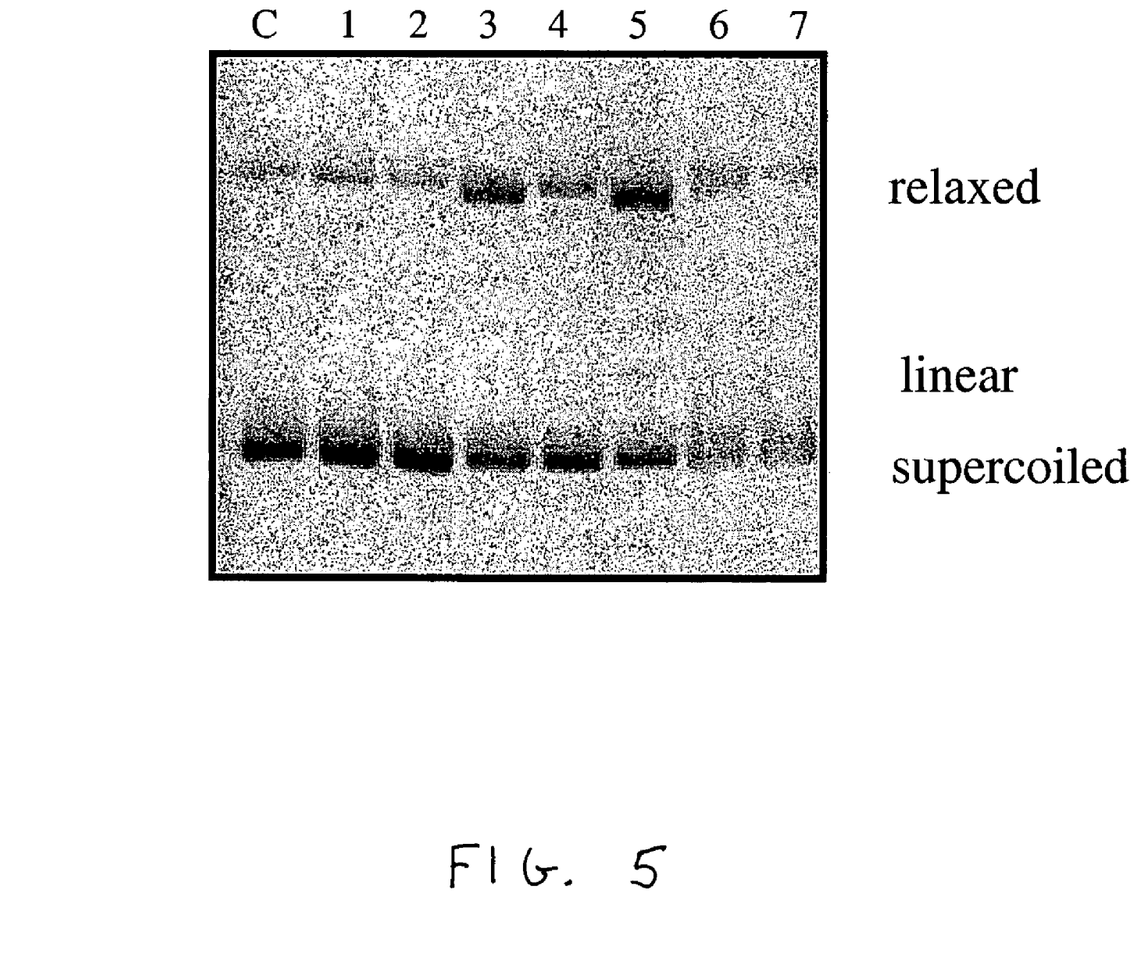
FIG. 5 depicts cleavage of supercoiled DNA by UK-1 in the presence of oxidizing agents and metal ions.

FIG. 5 depicts cleavage of supercoiled DNA by UK-1 in the presence of oxidizing agents and metal ions. Supercoiled ΦX174 DNA (50 μM bp) was incubated with UK-1 (23 μM), NiCl$_2$ (23 μM), H$_2$O$_2$ (5 mM), or combinations of these agents at 37° C. for 24 h and the DNA products subjected to agarose gel electrophoresis with ethidium bromide staining. Lanes: C, untreated supercoiled DNA; 1, DNA+UK-1; 2, DNA+NiCl$_2$; 3, DNA+H$_2$O$_2$; 4, DNA+UK-1+NiCl$_2$; 5, DNA+UK-1+H$_2$O$_2$; 6, DNA+UK-1+NiCl$_2$+H$_2$O$_2$; 7, DNA+NiCl$_2$+H$_2$O$_2$.

EXAMPLES

General. All reagents and solvents were purchased from Aldrich Chemical Company and used without further purification, unless noted. THF was distilled from sodium/benzophenone immediately prior to use. CH$_2$Cl$_2$ and DMF were distilled from CaH$_2$ immediately prior to use. Toluene was distilled from sodium metal. UV/V is spectra for the continuous variation plots were determined on a Varian Cary 3E spectrophotometer. Melting points (open capillary) are uncorrected. Unless otherwise noted, $^1$H and $^{13}$C NMR spectra were determined in CDCl$_3$ on a spectrometer operating at 300 and 75.5 MHz, respectively. All mass spectra were obtained by chemical ionization using methane as the ionizing gas. Chromatography refers to flash chromatography on silica gel, and Rf values were determined using silica gel-GF TLC plates (Merck) using the solvent system indicated.

2.4

Compound 2.3: Methyl 2-{[2-(benzyloxy)benzoyl]amino}-3-hydroxybenzoate. Carbonyldiimidazole (CDI) (5.10 g, 31.5 mmol) was dissolved in 50 ml dry THF with stirring at room temperature under an argon atmosphere, and 2-(benzyloxy)benzoic acid (compound 2.4) (7.18 g, 31.5 mmol) was added to the mixture. After the evolution of CO$_2$ ceased (ca. 5 min) the reaction mixture was stirred for an additional 10 minutes and methyl 2-amino-3-hydroxybenzoate (3.5 g, 21 mmol) was added. After stirring for an additional 10 minutes at room temperature, the reaction mixture was heated under reflux for 18 hours. The reaction mixture, brown in color, was concentrated and dissolved in a minimum volume of ethyl acetate (EtOAc). Silica gel (60-100 mesh) was added to make a slurry and solvent was evaporated to dryness. Column chromatography was performed using 20% EtOAc in hexane to give a light yellow solid (6.9 g, 87%): mp 104-105° C.; R$_f$ 0.328 (20% EtOAc in hexanes); $^1$H NMR δ 3.80 (s, 3H), 5.50 (s, 2H), 7.05 (d, 1H, J=8.1 Hz), 7.10 (t, 1H), 7.24 (m, 2H), 7.34 (m, 3H), 7.47 (m, 3H), 7.61 (d, 1H, J=7.8 Hz),8.27 (d, 1H, J=9.0 Hz), 9.28 (brs, 1H, NH), 12.27 (s, 1H, OH); $^{13}$C NMR δ 52.20, 70.80, 113.34, 120.94, 121.27, 121.58, 122.97, 125.70, 126.05, 126.93, 128.01, 128.21, 128.60, 132.69, 133.93, 136.22, 150.76, 157.01, 165.51, 167.57; CIMS m/z 378 (MH+); HRMS m/z calc'd for C22H20NO5: 378.1341, found 378.1343.

2.5

Compound 2.5: Methyl 2-[2-(benzyloxy)phenyl]-1,3-benzoxazole-4-carboxylate. Compound 2.3 (6.9 g, 1.83 mol) was heated neat at 230° C. for 2 hours with stirring in a long neck 50 ml round bottomed flask under vacuum, which was applied slowly at small intervals (20 minutes) to remove the water vapor generated in the reaction. Upon cooling, a light orange solid mass was obtained, which was dissolved in a minimum volume of EtOAc. To this solution, hexane was added with stirring to precipitate the product benzoxazole, which was filtered to give a white solid (6.0 g, 91%): mp 100-102° C.; $R_f$ 0.468 (40% EtOAc in hexanes); $^1$H NMR δ 3.99 (s, 3H), 5.28 (s, 2H), 7.07 -7.13 (m, 2H), 7.27-7.33 (m, 1H), 7.35-7.42 (m, 3H), 7.48 (ddd, 1H, J=7.8, 1.7 (br d, 1H), 7.73 (dd, 1H, J=8.1, 1.0 Hz), 8.02 (dd, 1H, J=7.8,1.2,1.0 Hz), 8.25 (br d, 1H); $^{13}$C NMR δ 52.40, 70.56, 113.61, 114.67, 116.31, 121.03, 121.98, 124.12, 126.79 (2C), 127.65, 128.45, 131.92, 133.19, 136.66, 141.46, 151.24, 157.74, 163.60, 165.97; CIMS m/z 360 (MH+); HRMS m/z calc'd for C22H18NO4: 360.1235, found 360.1228.

2.6

Compound 2.6: 2-[2-(benzyloxy)phenyl]-1,3-benzoxazole-4-carboxylic acid. Compound 2.5 (6.0 g, 1.67 mol) was dissolved in 80 ml of THF and 40 ml of 5M NaOH was added. The reaction mixture was stirred at 60° C. with stirring for 2 hours. The reaction mixture was cooled to room temperature, diluted with EtOAc and acidified with concentrated HCl. The organic layer was washed with brine two times and dried over anhydrous Na2SO4. The solvent was evaporated and the residue was dried under vacuum to afford a white solid that was recrystallized from EtOAc and hexanes (5.2 g, 90%): mp 103-104° C.; $R_f$ 0.15 (40% EtOAc in hexanes); $^1$H NMR δ 5.28 (s, 3H), 7.12-7.20(m, 2H), 7.37-7.49 (m, 4H), 7.52-7.60 (m, 3H), 7.77 (dd, 1H, J=7.9, 0.9 Hz), 8.14 (dd, 1H, J=7.6, 1.2 Hz), 8.21 (dd, 1H, J=7.8, 1.5 Hz); $^{13}$C NMR δ 70.98, 113.76, 114.61, 115.28, 120.07, 121.27, 125.48, 127.08, 127.31, 128.39, 128.90, 131.72, 134.44, 136.09, 141.13, 149.90, 158.27, 163.16, 165.00; CIMS m/z 346 (MH+); HRMS m/z calc'd for C21H16NO4: 346.1079, found 346.1078.

2.8

Compound 2.8: Methyl 2-amino-3-({[2-(2-benzyloxyphenyl)-1,3-benzoxazol-4-yl]carbonyl}aminobenzoate. To a solution of compound 2.6 (1.035 g, 3 mmol) in 40 ml of dry CH2Cl2 was added 10 ml of freshly distilled oxalyl chloride. After stirring for 10 minutes, 5 drops of DMF was added to the reaction mixture. The reaction mixture was stirred for 2 hours at room temperature and the solvent was removed by evaporation. The resultant yellow solid was dried under vacuum for 3 hours. The yellow solid was then dissolved in 15 ml of dry CH2Cl2 and transferred via canula to a solution of methyl 2,3-diaminobenzoate (compound 2.7)(498 mg, 3 mmol) dissolved in 20 ml of dry CH2Cl2 and 2 ml of pyridine. The reaction mixture was stirred at room temperature overnight and then diluted with CH2Cl2. The solution was washed with 1% HCl, satd. aq. NaHCO3 and satd. aq. NaCl. The organic layer was dried over anhydrous Na2SO4 and the solvent was evaporated to give the residue which was recrystallized from EtOAc to afford a light yellow solid (1.077 g, 73%): mp 178° C.; $R_F$ 0.447 (40% EtOAc in hexanes); $^1$H NMR δ 3.91 (s, 3H, CH3), 5.30 (s, 2H, CH2), 6.23 (brs, 2H, NH2), 6.75 (t, 1H, J=7.9 Hz),7.14-7.30 (m, 6H), 7.45-7.58 (m, 4H), 7.77 (dd, 1H, J=8.1, 0.7 Hz), 7.80 (dd, 1H, J=8.1, 1.5 Hz), 7.93 (dd, 1H, J=7.6, 1.2 Hz), 8.24 (dd, 1H, J=8.0, 1.7, 1.5 Hz), 8.28 (dd, 1H, J=7.6, 0.7 Hz), 10.64(s, 1H, NH); $^{13}$CNMR 651.59,70.89, 111.92, 113.94, 113.97, 115.46, 115.77, 121.28, 123.82, 124.74, 125.02, 125.87, 1126.83, 127.81, 128.23, 128.41, 129.37, 131.55, 133.75, 136.12, 139.45, 139.45, 144.36, 150.33, 157.87, 162.77, 162.82, 168.64; CIMS m/z 494 (MH+); HRMS m/z calc'd for C29H24N3O5: 494.1715, found 494.1711.

2.1

Compound 2.1: Methyl 2-[2-(2-hydroxyphenyl)-1,3-benzoxazol-4-yl]-1H-benz imidazole-4-carboxylate. Compound 2.8 (493 mg, 1 mmol) was dissolved in 20 ml of toluene and p-toluenesulfonic acid monohydrate (475 mg, 2.5 mmol) was added. The reaction mixture was refluxed for 2 hours and the solvent was distilled off. The residue was treated with CH$_2$Cl$_2$ and the solution was washed with satd. aq. NaHCO$_3$ and satd. aq. NaCl. The organic layer was dried over anhydrous Na$_2$SO$_4$ and the solvent was evaporated to give a solid, The solid was with EtOAc and filtered. The residue was dried and purified by preparative TLC using 40% EtOAc in hexanes to afford a white solid (200 mg, 68%): mp 243° C.; R$_F$ 0.170 (40% EtOAc in hexanes); $^1$H NMR δ 4.20 (s, 3H, CH$_3$), 7.10 (t, 1H, J=8.1, 7.2 Hz), 7.24 (d, 1H, J=8.4 Hz), 7.41 (t, 1H, J=7.8, 7.5 Hz), 7.52-7.61 (m, 2H), 7.74 (d, 1H, J=7.5 Hz), 8.02 (d, 1H, J=7.8 Hz), 8.09-8.14 (m, 2H), 8.56 (d, 1H, J=7.2 Hz), 10.53 (s, 1H, NH), 11.95 (brs, 1H, OH); $^{13}$C NMR δ 52.65, 109.97, 112.49, 113.88, 117.84, 119.20, 120.19, 122.61, 124.30, 125.71, 126.08, 127.87, 134.10, 134.45, 134.54, 137.65, 142.83, 149.23, 149.39, 158.54, 163.96, 166.64; CIMS m/z 386(MH$^+$); HRMS m/z calc'd for C$_{22}$H$_{16}$N$_3$O$_4$: 386.1141, found 386.1150.

2.11

Compound 2.11: Methyl 2-amino-3-{[2-(benzyloxy)benzoyl]amino}benzoate. Carbonyldiimidazole (compound 2.10) (2.43 g, 15 mmol) was dissolved in 30 ml dry THF with stirring under argon at room temperature and 2-(benzyloxy)benzoic acid (compound 2.2) (3.42 g, 15 mmol) was added to the mixture. Heavy evolution of CO$_2$ was observed for 3-4 min. After stirring for 10 minutes, methyl 2,3-diaminobenzoate (1.66 g, 10 mmol) was added and stirring continued further for 10 minutes. The reaction mixture was then heated under reflux for 5 days. The reaction mixture, dark brown in color, was concentrated and dissolved in a minimum volume of EtOAc. Silica gel (60-100 mesh) was added to make a slurry and the solvent was evaporated. The resulting solid was added to the top of a dry-packed chromatography column that was eluted with 20% EtOAc in hexane to give the product as a white solid (2.86 g, 76%): mp 111-113° C.; R$_F$ 0.373 (40% EtOAc in hexanes); $^1$H NMR δ 3.86 (s, 3H, CH$_3$), 5.25 (s, 2H, CH$_2$),5.58 (s, 2H, NH$_2$), 6.66 (t, 1H, J=8.0 Hz), 7.13-7.18 (m, 2H), 7.43-7.58 (m, 7H),7.75 (d, 1H, J=7.8 Hz), 8.27 (d, 1H, J=7.8 Hz), 9.20 (brs, 1H, NH); $^{13}$C NMR δ 51.68, 71.72, 112.57, 112.59, 116.10, 121.75, 121.83, 124.76, 128.49, 128.77, 129.12 (2C), 130.09, 132.72, 133.32, 135.01, 144.51, 156.54, 163.98, 168.40; CIMS m/z 377 (MH$^+$); HRMS m/z calc'd for C$_{22}$H$_{21}$N$_2$O$_4$: 377.1501, found 377.1499.

2.12

Compound 2.12: Methyl 2-[2-(benzyloxy)phenyl]-1H-benzimidazole-4-carboxylate. Compound 2.11 (2.86 g, 76 mmol) was heated in glacial acetic acid (20 ml) at 120° C. for 30 minutes with stirring in a 50 ml round bottom flask. The reaction mixture was allowed to cool and then poured into ice cold water and extracted with CH$_2$Cl$_2$. The combined organic layers were washed with satd. aq. NaHCO$_3$, brine and dried (Na$_2$SO$_4$). The solvent was removed by evaporation and the residue was purified by chromatography on silica gel (60-100 mesh) using 20 to 40% EtOAc in hexane to afford benzimidazole ester 8 as a white solid (2.3 g, 80%): mp 100-101° C.; R$_F$ 0.412 (40% EtOAc in hexanes); $^1$H NMR δ 3.67 (s, 3H, CH$_3$), 5.36 (s, 2H, CH$_2$), 7.17-7.23 (m, 2H), 7.33 (t, 1H, J=7.7 Hz), 7.40-7.49 (m, 4H), 7.56 (dd, 2H, J=7.6, 1.7 Hz), 7.90 (dd, 1H, J=7.6, 1.0 Hz),8.03 (d, 1H, J=8.4 Hz), 8.62 (dd, 1H, J=7.8, 1.8 Hz), 11.56 (brs, 1H); $^{13}$C NMR δ 51.69, 71.29, 112.95, 113.40, 117.93, 121.68, 121.90, 124.30, 124.52, 127.95, 128.51, 128.92, 130.51, 131.58, 134.16, 135.64, 143.74, 150.91, 156.33, 166.33; CIMS m/z 359 (MH$^+$); HRMS m/Z calc'd for C$_{22}$H$_{19}$N$_2$O$_3$: 359.1395, found 358.1393.

2.9

Compound 2.9: 2-[2-(benzyloxy)phenyl]-1H-benzimidazole-4-carboxylic acid. Compound 2.12 (1.0 g, 2.78 mmol) was dissolved in 20 ml of THF and 8 ml of 5M NaOH was added. The reaction mixture was stirred at 60° C. for 3 hours. The reaction mixture was allowed to cool to room temperature and acidified with concentrated HCl. The obtained white solid was filtered, washed with water, and dried under vacuum to afford the acid 9 (780 mg, 81%): mp 188° C.; $R_f$ 0.125 (40% EtOAc in hexanes); $^1$H NMR (DMSO-$d_6$) δ 5.32 (s, 2H, CH$_2$), 7.15 (t, 1H, J=7.5), 7.29-7.41 (m, 5H), 7.49 (t, 1H, J=8.1 Hz), 7.56 (d, 2H, J=7.4 Hz), 7.78 (d, 1H, J=7.7 Hz), 7.92 (d, 1H, J=7.5 Hz), 8.32 (dd, 1H, J=7.9, 1.8 Hz), 11.85 (brs, 1H); $^{13}$C NMR (DMSO-$d_6$) δ 70.27, 107.28, 114.01, 117.73, 121.49, 121.66, 124.21, 123,68, 127.85, 128.12, 128.64, 130.00, 131.80, 134.68, 136.13, 141.02, 150.23, 155.89, 167.11; CIMS m/z 345 (MH$^+$); HRMS m/z calc'd for $C_{22}H_{17}N_2O_3$: 345.1239, found 345.1233

2.13

Compound 2.13: Methyl 2-(2-hydroxyphenyl)-benzoxazole-4-carboxylate. Compound 2.3 (103 mg, 0.3 mmol) was dissolved in 4 ml of toluene and p-toluenesulfonic acid monohydrate (142 mg, 0.75 mmol) was added. The reaction mixture was refluxed for 1.5 hours and, after cooling to room temperature, was diluted with EtOAc. The organic layer was washed with satd. aq. NaHCO$_3$ and satd. aq. NaCl, dried over anhydrous Na$_2$SO$_4$, and the solvent was evaporated to afford the benzoxazole as a solid (45 mg, 58%): mp 134-135° C.; $R_f$ 0.578 (30% EtOAc in hexanes); $^1$H NMR δ 4.05 (s, 3H, CH$_3$), 7.01 (t, 1H), 7.13 (d, 1H, J=8.1 Hz), 7.4-7.5(m, 2H), 7.78 (d, 1H, J=8.1 Hz), 8.01 (d, 1H, J=7.5 Hz), 8.06 (d, 1H, J=8.1 Hz); $^{13}$C NMR δ 52.38, 109.91, 114.86, 117.63, 119.55, 121.24, 124.69, 127.15, 127.40, 134.19, 139.36, 149.70, 159.33, 164.26, 165.52; CIMS m/z 270 (MH$^+$); HRMS m/z calc'd for $C_{15}H_{12}NO_4$: 270.0766, found 270.0766.

2.14

Compound 2.14: Methyl 3-hydroxy-2-{[2-(benzyloxyphenyl)-1,3-benzoxazol-4-yl]carbonyl}aminobenzoate. To a solution of compound 2.6 (3.45 g, 10 mmol) in 60 ml of dry CH$_2$Cl$_2$ was added 10 ml of freshly distilled oxalyl chloride. The reaction mixture was stirred for 10 minutes and 0.3 ml of dimethyl formamide was added to initiate the reaction. The reaction mixture was stirred for 2 hours at room temperature and the solvent was removed by evaporation. The resultant yellow solid was dried under vacuum for 3 hours. The yellow solid was then dissolved in 20 ml of dry CH$_2$Cl$_2$ and transferred via cannula to a solution of methyl 2-amino-3-hydroxybenzoate (1.67 g, 10 mmol) dissolved in 40 ml of dry CH$_2$Cl$_2$ and 3 ml of pyridine. The reaction mixture was stirred at room temperature overnight and then diluted with dichloromethane. The solution was washed with 1% HCl, satd. aq. NaHCO$_3$ and satd. aq. NaCl. The organic layer was dried over anhydrous Na$_2$SO$_4$ and the solvent was evaporated to give a residue which was subjected to column chromatography using CH$_2$Cl$_2$ as eluent to afford a light yellow solid (3.8 g, 77%): mp 157-158° C.; $R_f$ 0.329 (CH$_2$Cl$_2$); $^1$H NMR δ 3.79 (s, 3H), 5.29 (s, 2H), 7.13-7.39 (m, 8H), 7.50-7.55 (m, 4H), 7.65 (dd, 1H, J=7.5, 1.5 Hz), 7.80 (brd, 1H, J=8.1 Hz), 8.31 (brd, 1H, J=7.8 Hz), 8.50 (dd, 1H, J=7.5, 1.8 Hz); $^{13}$C NMR δ 52.23, 70.71, 113.76, 114.71, 115.76, 121.18, 122.51, 122.98, 123.62, 124.73, 125.62, 126.35, 126.50, 126.69, 127.68, 127.87, 132.31, 133.66, 136.28, 139.91, 150.87, 151.20, 157.89, 163.46, 164.40, 167.11; CIMS m/z 495 (MH$^+$); HRMS m/z calc'd for $C_{29}H_{23}N_2O_6$: 495.1556, found 495.1553.

2.15

Compound 2.15: Methyl 2'-(3-benzyl-2-hydroxyphenyl)-2,4'-bi-1,3-benzoxazole-4-carboxylate. A mixture of dry toluene (20 ml) and p-toluenesulfonic acid monohydrate (950 mg, 5 mmol) was refluxed under a reflux condenser. Compound 2.14 (988 mg, 2 mmol) was added and the reaction mixture was refluxed for an additional 2 hours. After the solvent was removed by distillation, the residue was dissolved in $CH_2Cl_2$ and the solution was washed with satd. aq. $NaHCO_3$ and satd. aq. NaCl. The organic layer was dried over anhydrous $Na_2SO_4$ and the solvent was evaporated to give 432 mg of solid that was a mixture of UK-1 and compound 2.15 (TLC and $^1$H NMR) in the ratio of 1.6:1.0. Column chromatography using 5 to 20% EtOAc in hexane afforded 10 mg pure compound 2.15 (1%) along with 300 mg UK-1 (13%) and a large mixed fraction (122 mg). Compound 2.15: mp 204-205° C.; $R_f$ 0.357 (30% EtOAc in hexanes); $^1$H NMR δ 4.09 (s, 3H, $CH_3$), 4.15 (s, 2H, $CH_2$), 6.96 (t, 1H, J=7.6 Hz, $C_5$—H), 7.20-7.14 (m, 1H, $C_3$-benzyl-H(para)), 7.26 (s, 2H, $C_3$-benzyl-H(meta)), 7.27 (s, 2H, $C_3$-benzyl-H(ortho)), 7.30 (dd, 1H, J=7.5, 1.2 Hz, $C_4$—H), 7.46 (t, 1H, J=7.9 Hz, $C_6$—H), 7.52 (t, 1H, J=8.0 Hz, $C_6$'-H), 7.77 (dd, 1H, J=8.1, 1.0 Hz, $C_7$'-H), 7.86 (dd, 1H, J=8.1, 1.0 Hz, $C_7$—H), 7.96 (dd, 1H, J=7.9, 1.6 Hz, $C_6$—H), 8.10 (dd, 1H, J=7.7, 1.0 Hz, $C_5$—H), 8.31 (dd, 1H, J=7.8, 0.9 Hz, $C_5$'-H); $^{13}$C NMR δ 35.83, 52.63, 109.72, 113.82, 115.09, 117.61, 119.33, 122.57, 124.93, 125.11, 125.24, 125.51, 126.07, 127.57, 128.42, 128.81, 129.77, 135.26, 138.76, 140.38, 141.56, 150.01, 151.22, 157.65, 161.71, 165.05, 166.32: CIMS m/z 477 (MH$^+$); HRMS m/z calc'd for $C_{29}H_{21}N_2O_5$: 477.1450, found 477.1442.

Compound 2.16: Methyl 2-(2-Hydroxy-phenyl)-benzooxazole-7-carboxylate. To a solution of 2-benzyloxybenzoic acid dry $CH_2Cl_2$ was added to 1 ml of freshly distilled oxalyl chloride. After stirring for 10 minutes, 1 drop of DMF was added to the reaction mixture. The reaction mixture was stirred for 2 hours at room temperature and the solvent was removed by evaporation. The resultant yellow oil was dried under vacuum for 3 hours. The yellow oil was then dissolved in 5 ml of dry xylenes and transferred via cannula to a solution of 3-aminosalacylic acid (g, 31.5 mmol) in xylenes. The mixture was stirred at room temperature for 1 h, then heated to reflux overnight. After the reaction mixture had cooled to room temperature, p-toluenesulfonic acid monohydrate (475 mg, 2.5 mmol) was added and the mixture heated to reflux for an additional 12 h. The reaction mixture was cooled to 0° C. and treated with an excess of $TMSCHN_2$. The product was purified by column chromatography (20% EtOAc in hexane) to give a light yellow solid (42 mg, 36%): $^1$H NMR δ 4.04 (s, 3H, $CH_3$), 7.00 (m, 1H), 7.10 (d, 1H, J=8.4 Hz), 7.4-7.5 (m, 2H), 7.87 (dd, 1H, J=8.1, 1.2 Hz), 7.97 (dd, 1H, J=7.5, 1.2 Hz), 8.06 (dd, 1H, J=8.1, 1.2 Hz); CIMS m/z 270 (MH$^+$); HRMS m/z calc'd for $C_{15}H_{12}NO_4$: 270.0763, found 270.0766.

Cytotoxicity Assays. Cell culture cytotoxicity assays were performed using the. alamarBlue method, as described by Ahmed et al., *J. Immun. Methods* 1994, 170, 211-224, which is incorporated herein by reference. Briefly, aliquots of 100 μL of cell suspension (1.0-2.5×10$^3$ cells) was placed in 96-well microtiter plates in an atmosphere of 5% $CO_2$ at 37° C. After 24 hours, 100 μL of culture medium and 2 μL of compound in vehicle (culture media with 40% pyridine) or vehicle alone were added, and the plates incubated an additional 72 hours. The final pyridine concentration in all cases was 0.4%; at this pyridine concentration there was no affect on the growth of cells compared to cells in culture media without added pyridine. Compounds, along with mitomycin C as positive control, were evaluated in duplicate at final concentrations ranging from 0.001 to 100 μM. After the culture media had been removed from each well, 200 μL of fresh media and 20 μL of 90% alamarBlue reagent were added, followed by an additional 6 h incubation. The fluorescent intensity was measured using a Spectrafluor Plus plate reader with excitation at 530 nm and emission at 590 nm. Results are reported as $IC_{50}$ values, the average concentration required to produce a decrease of fluorescent intensity of 50% relative to vehicle-treated controls in two separate determinations.

Antimicrobial Bioassay: *Staphylococcus aureus* ATCC 29213 and methicillin-resistant *S. aureus* ATCC 43300 (MRS) were obtained from the American Type Culture Collection (Rockville, Md.) and stored on agar slants at 4° C. until needed. Susceptibility testing was performed using a modified version of the NCCLS methods: "Methods for Dilution Antimicrobial Susceptibility Tests for Bacteria that Grow Aerobically," M7-A4, Vol. 17, No. 2, NCCLS, (1997) and "Reference Method for Broth Dilution Antifungal Susceptibility Testing of Yeasts; Approved Standard," M27-A, Vol. 17, No. 9, NCCLS, (1997), both of which are incorporated herein by reference. Microorganisms were subcultured prior to the assay by suspending cells from the slant in Eugon broth (BBL, Maryland) and incubating for 24 hours at 37° C. Inocula were prepared by diluting the subcultured organism in its incubation broth after comparison to the 0.5 McFarland Standard (a $BaSO_4$ suspension) to afford final inocula ranges of *S. aureus*: 1.0-5.0×10$^5$ and MRS: 0.2-6.0× 10$^5$ CFU/ml. Test compounds were dissolved in DMSO, serially-diluted using normal saline, and transferred in duplicate to 96 well flat-bottomed microtiter plates. The microbial inocula were added to the samples to achieve a final volume of 200 μl and final compound concentrations starting with 50 μg/ml. Drug [Ciprofloxacin (ICN Biomedicals, Ohio)] as well as growth and blank (media only) controls were added to each test plate. Plates were read at 630 nm using the EL-340 Biokinetics Reader (Bio-Tek Instruments, Vermont) prior to and after incubation at 37° C. for 24 hours. Percent growth was calculated and plotted versus concentration to afford the $IC_{50}$, or sample concentration that affords 50% growth of the organism relative to controls.

Continuous variation plots. A 100 μM solution of UK-1 or analogue and 100 AM solutions of $Ca(NO_3)_2$, $Mg(NO_3)_2$, $Zn(NO_3)_2$, or $Fe(NO_3)_3$ were prepared in methanol. From these stock solutions, 15 samples (1 mL) of varying mole fraction of the metal ion were prepared at a constant, combined concentration of 20 μM for the ligand and the metal ion. The change in absorbance was monitored from 500 to 200 nm for each sample using as a reference a 1 mL solution containing the same concentration of ligand as the sample being measured but without the metal ion. The maximum absorbance change was typically around 418 nm but varied somewhat for each metal ion. The absorbance at 418 nm was plotted as a function of the mole fraction of the metal ion and the maximum absorbance change was determined. The absorbance of a sample containing the metal ion concentration corresponding to this maximum change and a 15 fold excess of metal ion at this ligand concentration, subtracted from a reference containing the same concentration of ligand but no metal ion was used to normalize the curve and obtain the conditional formation constant as described in the paper to Likussar, W.; Boltz, D. F. *Anal. Chem.* 1971, 43, 1265-1272, which is incorporated herein by reference.

While the present invention has been described with reference to particular embodiments, it will be understood that the embodiments are illustrated and that the invention scope is not so limited. Any variations, modifications, additions and improvements to the embodiments described are possible. These variations, modifications, additions and improvements may fall within the scope of the invention as detailed within the following claims.

What is claimed is:

1. A method of synthesizing a chemical compound comprising a cyclic ring having the structure II where $R^1$ is alkyl or aryl;
where each $R^2$ is independently hydrogen, alkyl, aryl, or halogen;
where n is 1 to 4; and
where X is N and Y is O, comprising:
reacting an acyclic compound having the structure III with an acid in a hydrocarbon solvent;

where $R^1$ and $R^2$ are independently hydrogen, alkyl, aryl, or halogen;
where n is 1 to 4; and
where X and Y are independently N or O; heating the reaction.

2. The method of claim 1, wherein the acid is an organic acid.
3. The method of claim 1, wherein the acid is p-TsOH.
4. The method of claim 1, wherein the solvent is an organic solvent.
5. The method of claim 1, wherein heating the reaction comprises a temperature above 80° C.
6. The method of claim 1, further comprising cooling the reaction down to at least room temperature and filtering off the acid.

* * * * *

UNITED STATES PATENT AND TRADEMARK OFFICE
CERTIFICATE OF CORRECTION

| | | |
|---|---|---|
| PATENT NO. | : 7,294,643 B2 | Page 1 of 1 |
| APPLICATION NO. | : 10/720991 | |
| DATED | : November 13, 2007 | |
| INVENTOR(S) | : Sean M. Kerwin | |

It is certified that error appears in the above-identified patent and that said Letters Patent is hereby corrected as shown below:

In the specification please add:

Line 3; column 1

STATEMENT REGARDING FEDERALLY SPONSORED RESEARCH OR DEVELOPMENT

"This invention was made with government support under Grant no. GM050892 awarded by the National Institutes of Health. The government has certain rights in the invention."

Signed and Sealed this
Twenty-sixth Day of May, 2015

Michelle K. Lee
*Director of the United States Patent and Trademark Office*